United States Patent [19]

Rudnic et al.

[11] Patent Number: 5,484,608

[45] Date of Patent: Jan. 16, 1996

[54] SUSTAINED-RELEASE DRUG DELIVERY SYSTEM

[75] Inventors: Edward M. Rudnic, No. Potomac, Md.; John A. McCarty, Biscayne Park, Fla.; George W. Belenduik, Potomac, Md.

[73] Assignee: Pharmavene, Inc., Rockville, Md.

[21] Appl. No.: 218,757

[22] Filed: Mar. 28, 1994

[51] Int. Cl.$^6$ ................ A61K 9/22; A61K 9/24; A61K 9/26

[52] U.S. Cl. ............ 424/468; 424/457; 424/459; 424/461; 424/462; 424/469; 424/476; 424/487; 424/489; 424/490; 424/493; 424/497; 424/502; 514/54; 514/60; 514/317; 514/646; 514/647; 514/965

[58] Field of Search ............... 514/54, 60, 317, 514/646, 647, 965; 424/457, 459, 461, 462, 489, 490, 493, 502, 468, 469, 476, 487, 497

[56] References Cited

U.S. PATENT DOCUMENTS

| | | | |
|---|---|---|---|
| 4,140,755 | 2/1979 | Sheth et al. | 424/468 |
| 4,330,338 | 5/1982 | Banker | 106/170 |
| 4,333,919 | 6/1982 | Kleber et al. | 424/442 |
| 4,351,825 | 9/1982 | Sothmann et al. | 424/490 |
| 4,610,870 | 9/1986 | Jam et al. | 424/19 |
| 4,629,621 | 12/1986 | Snipes | 428/402.24 |
| 4,731,241 | 3/1988 | Yamada et al. | 514/227 |
| 4,812,481 | 3/1989 | Reischig et al. | 514/661 |
| 4,861,598 | 8/1989 | Oshlack | 424/469 |
| 4,999,189 | 3/1991 | Kogan et al. | 514/781 |
| 5,055,304 | 10/1991 | Makino et al. | 424/502 |
| 5,126,145 | 6/1992 | Evenstad et al. | 424/465 |
| 5,151,419 | 9/1992 | Perenyi et al. | 514/646 |
| 5,192,550 | 3/1993 | Edgren et al. | 424/473 |
| 5,338,550 | 8/1994 | Edgren et al. | 424/473 |

OTHER PUBLICATIONS

Physician's Desk Reference (1995), pp. 2430–2432.

*Primary Examiner*—Ronald W. Griffin
*Attorney, Agent, or Firm*—Charles J. Herron; Elliot M. Olstein

[57] ABSTRACT

A sustained-release pharmaceutical composition comprising a highly soluble pharmaceutical agent, such as selegiline, in a pharmaceutical carrier comprising a hydrophilic polymer dispersed in a hydrophobic matrix. A hydrophilic microenvironment is created in a hydrophobic matrix by incorporating hydrophilic polymers within a hydrophobic matrix. Optionally, a binder, preferably a polyhydroxylated compound, ca also be added.

10 Claims, 1 Drawing Sheet

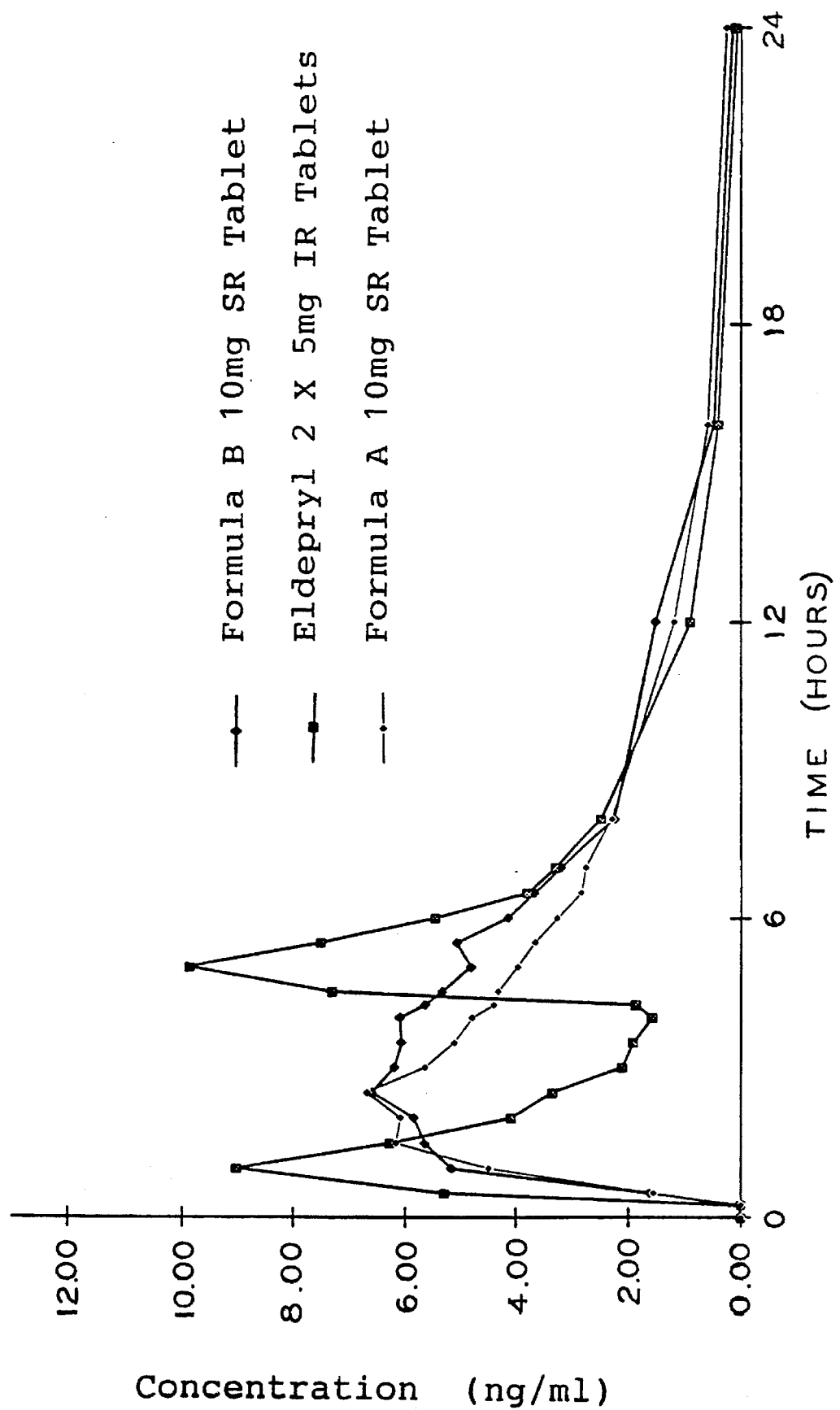

SUSTAINED-RELEASE DRUG DELIVERY SYSTEM

The present invention relates to sustained-release pharmaceutical carriers, particularly to pharmaceutical carders formulated to provide for the reliable sustained-release of highly water soluble pharmaceutical agents.

Highly water soluble compounds present the problem that traditional matrix controlled-release systems using hydrophilic polymers do not properly control the rate of release of such compounds from the dosage form. Most approaches for these highly soluble drugs would require a rate-controlling coating over any conventional matrix dosage form.

Water soluble compounds are those molecules that require 30 or less pans of water (solvent) to dissolve one pan of drug (solute). The United States Pharmacopoeia uses the descriptive terms "soluble" to mean from 10 to 30 pans solvent to dissolve one part solute, "freely soluble" to mean from 1 to 10 pans solvent to dissolve one part solute and "very soluble" to mean that less than one pan solvent is needed to fully dissolve one part solute. For the purposes of this invention, all freely and very soluble compounds can benefit from this drug delivery system. However, those drugs that are either very soluble or approach "very soluble" are especially suitable for this invention.

By utilizing lipophilic components only in the matrix, release of highly water soluble drugs would be dependent on erosion in the gastrointestinal tract, and probably could not be reliably achieved to deliver the drug over a five-hour period. Such a system could be expected to release the drug from as little as two hours to twelve hours in vivo.

One particularly preferred pharmaceutical agent for incorporation into the composition of the invention to permit reliable sustained-release is selegiline hydrochloride, a type B-selective monoamine oxidase (MAO) inhibitor. It is indicated as an adjunct in the management of Parkinson's disease patients being treated with levodopa/carbidopa. Selegiline (formerly called L-deprenyl) is (R)-(-)-N, 2-dimethyl-N-2-propynylphenethylamine.

The hydrochloride salt is marketed as an immediate-release (IR) tablet in the United States as Eldepryl™ (Somerset Pharmaceuticals) and internationally as lurnex. The free-base is internationally marketed as Eldèprine, and Movergan. Selegiline hydrochloride (Eldepryl™), a highly potent, irreversible inhibitor of MAO-B, was developed in 1964 as a "psychic energizer" by Dr. Knoll in Hungary (Knoll et al., 1965, 1983, 1989).

Selegiline is rapidly absorbed, with maximum blood levels reached at 1 hour after oral administration (Elsworth et al., 1978). Its average plasma half-life is approximately 40 hours. A dose of 5 mg inhibits 90 to 100% platelet MAO-type B activity, and 10 mg inhibits 100%. After stopping the drug, activity is inhibited greater than 50% at 1 week and does not return to normal until 2 to 3 weeks (Maitre et al., 1976). Selegiline readily enters the brain, but a dose of 10 mg does not appear to completely inhibit brain MAO-type B (Golbe et al., 1988).

Following the oral administration of a single 10 mg dose of selegiline to 11 healthy subjects, serum levels of intact selegiline were below the limit of detection (less than 10 ng/ml). Three metabolites, N-desmethylselegiline, the major metabolite (mean $t_{1/2}$ of 2 hours), amphetamine (mean $t_{1/2}$ of 17.7 hours) and methamphetamine (mean $t_{1/2}$ of 20.5 hours) were found in serum and urine. Over a period of 48 hours, 45% of the dose administered appeared in the urine as these 3 metabolites. In a longer study, these subjects were given a 10 mg dose of selegiline for 7 consecutive days. The mean trough serum levels for amphetamine were 3.5 ng/ml and 8.0 ng/ml for methamphetamine; trough levels of N-desmethyl selegiline were below levels of detection (Eldepryl™ Package Insert, 1991; Magyar and Tothfalusi, 1984). Heinonen and colleagues measured mean concentration levels of metabolites in serum and cerebrospinal fluid (CSF) in 21 patients on continuous selegiline therapy for an average of 23 months. Mean CSF concentrations, similar for serum and CSF, were 6.5+/-2.5 ng/ml for L-amphetamine, 14.7+/- 6.5 ng/ml for methamphetamine, and 0.9+/-0.7 ng/ml for desmethyl selegiline. Eighty-seven percent of the parent drug was recovered as metabolites in the urine (Heinonen et al., 1989c). Post-mortem studies in human brain tissue have shown that after Eldepryl™ administration to parkinsonian patients, amphetamine is present in concentrations up to 56 ng/ml (Reynolds et al., 1978).

In humans, the half-life times appear to be much greater, up to 40 hours, than in the dog values (up to 8 hours) (Eldepryl™ Summary Basis of Approval, NDA No. 19-334). Drug plasma concentrations are difficult to assess due to 1) the metabolism of drug to its metabolites which have different plasma time courses and pharmacological actions, 2) all metabolites have not been identified and tested for activity, 3) all effects of selegiline are mediated by the MAO-B turnover time, and (4) levels of metabolites are difficult to assay.

Other drugs that are contemplated include, but are not limited to: bleomycin sulfate, captopril, chlorpheniramine maleate, chlorpromazine HCl, clindamycin HCl, codeine phosphate, colistin sulfate, cytarabine, diltiazem HCl, ephedrine sulfate, meperidine HCl, nadolol, procainamide HCl, tetracaine HCl, thiamine HCl and tobramycin.

Many of such highly water soluble pharmaceutical agents had not previously been susceptible to sustained-release as their high degree of solubility cause the entire dose of the compound to dissolve and thus be delivered immediately. This required the delivery of small doses many times per day. There remains a significant need for a pharmaceutical carrier preparation that will make it possible to administer even such highly soluble pharmaceutical agents on a sustained-release basis as infrequently as once a day.

In accordance with the present invention there is provided a sustained-release pharmaceutical composition comprising a pharmaceutical agent in a pharmaceutical carrier comprising a hydrophilic polymer dispersed in a hydrophobic matrix. A hydrophilic microenvironment is created in a hydrophobic matrix by incorporating hydrophilic polymers within a hydrophobic matrix.

Hydrophilic polymers that are useful in the invention include, but are not limited to hydroxypropylmethylcellulose (HPMC), hydroxypropylcellulose (HPC), hydroxyethylcellulose (HEC), carboxymethylcellulose (CMC) or other cellulose ethers, or acrylic acid derivatives such as polyacrylic acid, Carbopol 934P(B. F. Goodrich, Cleveland, Ohio), block copolymers of ethacrylic and methacrylic acid esters, Eudragit RL, RS, R, S, and E (Rhome Pharma, Darmstadt, Germany), acrylic acid polymer, methacrylic acid polymer, hydroyethyl methacrylic acid (HEMA) polymer or hydroxymethyl methacrylic acid (HMMA) polymer. The most preferred hydrophilic polymer is Carbopol 934P.

Hydrophobic, or lipophilic, components that are useful in the invention include, but are not limited to, glyceryl monstearate, mixtures of glyceryl monostearate and glyceryl monopalmitate (Myvaplex, Eastman Fine Chemical Company), glycerylmonooleate, a mixture of mono, di and tri-glycerides (ATMUL 84S), glycerylmonolaurate, paraffin, white wax, long chain carboxylic acids, long chain carboxylic acid esters and long chain carboxylic acid alcohols.

The long chain carboxylic acids, generally contain from 6–30 carbon atoms and preferably contains at least 12 carbon atoms, most preferably 12 to 22. In some cases this carbon chain is fully saturated and unbranched, while others contain one or more double bonds. A few contain 3-carbon rings or hydroxyl groups. Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain monocaboxyic acids. Examples of these are linoleic acid, linolenic acid, arachidonic acid and behenolic acid. Useful branched acids include, for example, diacetyl tartaric acid.

Examples of long chain carboxylic acid esters include, but are not limited to, those from the group of: glyceryl monostearates; glyceryl monopalmitates; mixtures of glyceryl monostearate and glyceryl monopalmitate (Myvaplex 600, Eastman Fine Chemical Company); glyceryl monolinoleate; glyceryl monooleate; mixtures of glyceryl monopalmitate, glyceryl monostearate glyceryl monooleate and glyceryl monolinoleate (Myverol 18-92, Eastman Fine Chemical Company); glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate (Myverol 18-99, Eastman Fine Chemical Company); acetylated glycerides such as distilled acetylated monoglycerides (Myvacet 5-07, 7-07 and 9-45, Eastman Fine Chemical Company); mixtures of propylene glycol monoesters, distilled monoglycerides, sodium stearoyl lactylate and silicon dioxide (Myvatex TL, Eastman Fine Chemical Company); mixtures of propylene glycol monoesters, distilled monoglycerides, sodium stearoyl lactylate and silicon dioxide (Myvatex TL, Eastman Fine Chemical Company) d-alpha tocopherol polyethylene glycol 1000 succinate (Vitamin E TPGS, Eastman Chemical Company); mixtures of mono- and diglyceride esters such as Atmul (Humko Chemical Division of Witco Chemical); calcium stearoyl lactylate; ethoxylated mono- and di-glycerides; lactated mono- and di-glycerides; lactylate carboxylic acid ester of glycerol and propylene glycol; lactyic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; cetearyl octanoate; $C_{10}$–$C_{30}$ cholesterol/lavosterol esters; and sucrose long chain carboxylic acid esters.

The alcohols useful in the invention are exemplified by the hydroxyl forms of the carboxylic acids exemplified above and also cetearyl alcohol.

In addition, waxes can be useful alone or preferably in combination with the materials listed above. Examples of these are white wax, paraffin and carnauba wax.

When the pharmaceutical composition is being prepared by wet mixing a binder can optionally be added to enhance the interaction of the hydrophilic and hydrophobic materials and to facilitate achieving the proper microenvironment to control the release of the highly soluble pharmaceutical agents. This binder binds the hydrophobic and hydrophilic regions together while causing hydrophilic channels within the hydrophobic matrix. Acacia is preferred among possible binders, but corn starch paste, modified or pre-gelatinized starches (STARCH 1500 and NATIONAL 1551) and dextrose, as well as hydroxypropylmethylcellulose (HPMC), hydroxypropylcellulose (HPC), or elthylcellulose (EC) can also be used. In addition, and less preferably, gum arabic, tragacanth, and guar gum can be used in this regard.

The binder preferably has multiple hydroxyl sites on its molecular structure in order to facilitate the appropriate hydrophilic/hydrophobic interaction necessary to maintain a suitable microenvironment to control and facilitate the sustained release of the pharmaceutical agent.

Also important is the nature of the hydrophobic ingredient. If the material is amphiphilic, or has surface-active properties, the binder does not need to have as many hydroxyl groups in its molecular structure. If the hydrophobic material is not wetted by water, the binder should have significant amounts of hydroxyl groups, and should possess substantial surface-active properties. The following examples are combinations of hydrophobic and hydrophilic balanced sustained-release matrix tablets.

EXAMPLE 1

Sustained Release Selegiline Formulation Tablets

| | |
|---|---|
| Selegiline HCl | 10.0% |
| Hydroxypropylmethylcellulose E50 | 5.0% |
| Hydroxypropylmethylcellulose K15M | 10.0% |
| Calcium phosphate dehydrate | 54.5% |
| ATMUL 84S | 20.0% |
| Magnesium stearate | 0.5% |

Combine the selegiline, a portion of each HPMC, calcium phosphate and Atmul 84S in a planetary mixer and dry mix for 15 minutes. Add a solution of the remainder of the HPMC in water to the mixer while mixing, until a wet mass is obtained. Pass the wet material through a screen to make the resultant granules of uniform size( to achieve uniform drying) and dry in an oven at 40° C. for 24 hours. Mill the dried granules through a Fitzpatrick Mill, knives forward, and collect the material in a mixer. Add the magnesium stearate and mix for 5 minutes. The resultant mixture is tabletted on a suitable tablet press.

EXAMPLE 2

Sustained Release Selegiline Formulation Tablets

| | |
|---|---|
| Selegiline HCl | 5.0% |
| Carbomer 934P, NF | 10.0% |
| Hydroxypropylmethylcellulose E50 | 20.0% |
| Calcium phosphate dihydrate | 59.5% |
| Glyceryl monstearate | 5.0% |
| Magnesium stearate | 0.5% |

Combine selegiline, Carbomer 934P, HPMC, calcium phosphate dihydrate and glyceryl monostearate to a planetary mixer and dry mix for 15 minutes. Add an aqueous solution of the remainder of the HMPC to the mixer while mixing, until a wet mass is obtained. Pass the wet material through a screen and dry in an oven at 40° C. for 24 hours. Mill the dried granules through a Fitzpatrick Mill, knives forward, and collect the material in a mixer. Add the magnesium stearate and mix for 5 minutes. The resultant mixture is tabletted on a suitable tablet press.

EXAMPLE 3

Sustained Release Selegiline Formulation Tablets

| | |
|---|---|
| Selegiline HCl | 2.5% |
| Carbomer 934P NF | 7.0% |
| Acacia NF | 29.0% |
| Calcium Sulfate NF | 56.0% |
| Glyceryl monostearate, USP/NF | 5.0% |
| Myvatex TL | 0.5% |

Combine the selegiline, Carbomer, calcium sulfate and glyceryl monostearate to form a dry mixture in a fluid-bed granulator(e.g. from Aeromatic or Glatt). Spray in the acacia in a lightly viscous aqueous solution to granulate(agglomerate) and dry the mixture. Add the magnesium stearate in a mixer for 5 minutes and tablet the mixture on a suitable tablet press.

EXAMPLE 4

Comparative N-Desmethylselegiline Plasma Level Profiles

Tablets were made to contain the components listed in Example 3 by two approaches(Formula A and Formula B). The difference between formula A and formula B is that formula B was processed by wet granulation, while formula A was produced using direct compression, a dry process. Eldepryl™ (5 mg tablets) was purchased.

Individuals from a group of eleven normal volunteers were randomly assigned to receive either Eldepryl™ (5 mg, twice a day), Formula A (10 mg, once a day) or Formula B (10 mg, once a day, for three days. This was followed by two weeks of no drug administration(during which plasma levels of n-desmethylselegiline fell to zero). The individuals were then rotated to recieve a different formulation for three days, followed by two weeks of no administration followed by three days of receiving the third formulation. At numerous intervals during each day of administration plasma was obtained from venipuncture blood samples and assayed for n-desmethylselegiline levels. Plasma concentration of n-desmethylselegiline can be measured by the method described in Patrick et al., J. Chromatog., 583:254–258(1992).

FIG. 1 shows the mean plasma profiles for n-desmethylselegiline concentrations (nanogram per ml of plasma). As can be seen from this figure, a very sensitive relationship exists between in vitro release rate and in vivo performance. Formula B has the more desirable performance for a once a day selegiline SR tablet.

This shows that a simple mixture of the ingredients (formula "A") is not sufficient to form the intricate microenvironment necessary for the sustained-release of selegiline. By incorporating the hydrophobic and hydrophilic components in a liquid binding process in the presence of a polyhydroxylated binder, a unique, and unexpected matrix microenvironment is produced in accordance with the invention.

Cited Literature

Elsworth, J. D., Glover, V., Reynolds, G. P., Sandler, M., Lees, A. J. Phuapradit, P., Shaw, K. M., Stern, G. M., Kumar, P., Deprenyl Administration in Man: A Selective Monoamine monoamine Oxidase B. Inhibitor Without the "Cheese Effect", *Psychopharmacology*, 57:33–38, 1978.

Golbe, L. I., Lieberman, A. N. and Muenter, M. D., et al., Deprenyl in the Treatment of Symptom Fluctuations in Advanced Parkinson's Disease, *Clin Neuropharmacol*, 11:45–55, 1988.

Heinonen, E. H., Myllyla, V., Sotaniemi, K., Lammintausta, R., Salonen, J. S., Anttila, M., Savijarvi, M., Kotila, M., Rinne, U. K., Pharmacokinetics and Metabolism of Selegiline, *Acta Neurol Scand.*, 126:93–99, 1989.

Knoll, J., Deprenyl (Selegiline): The History of Its Development and Pharmacological Action, *Acta Neural Scan.*, Supply 95:57–80, 1983.

Knoll, J., The Pharmcology of (–) Deprenyl, *J Neural Trans*, Suppl 22:75–89, 1986.

Knoll, J., The Pharmacology of Selegiline (–) Deprenyl: New Aspects, *Acta Neurol Scan*, 126:83–91, 1989.

Knoll, J., Ecseri, Z., Kelemen, K., Nievel, J., Knoll, B., phenylisopropylmethyl-propinylainine (E-250), a New Psychic Energizer, *Arch Int Pharmacodyn Ther*, 155:154, 164, 1965.

Maitre, I., Delini-Stula, A., and Waldmeier, P. C., (CIBA Foundation Symposium), New York: Elsevier, 247–270, 1976.

Magyar, K., Tothfalusi, L., Pharmacokinetic Aspects of Deprenyl Effects, *Pol J Pharmacol Pharm*, 36:373–384, 1984.

Reynolds, G. P., Riederner, P., Sandler, M., Jellinger, K., Seemann, D., Amphetamine and 2-Phenylethylamine in Post-Mortem Parkinsonian Brain after (–) Deprenyl Administration, *J Neural Transm*, 43:271–277, 1978,

What is claimed is:

1. A sustained-release pharmaceutical composition comprising a very soluble pharmaceutical agent in a pharmaceutical carrier comprising a hydrophilic polymer selected from the group consisting of acrylic acid polymers and polymers of derivatives thereof dispersed in a hydrophobic matrix.

2. The composition of claim 1 wherein a hydrophilic microenvironment is created in a hydrophobic matrix by incorporating the hydrophilic polymer within a hydrophobic matrix.

3. The composition of claim 1 wherein the hydrophilic polymer is selected from the group consisting of Carbomer 934P crosslinked acrylic acid polymer, block copolymers of ethacrylic and methacrylic acid esters. Eudragit RL copolymer of methacrylic acids, Eudragit RS copolymer of methacrylic acids. Eudragit S anionic copolymer of methacrylic acid and methacrylic acid methyl ester. Eudragit E cationic copolymer of dimethylaminoethyl methacrylate and neutral methacrylic acid esters, methacrylic acid polymer, hydroxyethyl methacrylic acid polymer and hydroxymethyl methacrylic acid polymer.

4. The composition of claim 1 wherein the hydrophobic component is selected from the group consisting of glyceryl monstearate, mixtures of glyceryl monostearate and glyceryl monopal reitate, glycerylmonooleate, mixtures of mono, di and tri-glycerides, glycerylmonolaurate, paraffin, white wax, long chain carboxylic acids, long chain carboxylic acid esters and long chain carboxylic acid alcohols.

5. The composition of claim 4 wherein the long chain carboxylic acid has from 6 to 30 carbon atoms.

6. The composition of claim 5 wherein the long chain carboxylic acid is selected from the group consisting of n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid, melissic acid, oleic acid, gadoleic acid, erucic acid, linoleic acid, linolenic acid, arachidonic acid, behenolic acid and diacetyl tartaric acid.

7. The pharmaceutical composition of claim 1 which further comprises a binder component effective to bind the hydrophilic polymer and the hydrophobic component.

8. The pharmaceutical composition of claim 7 wherein the binder component is selected from the group consisting of acacia, corn starch paste, modified or pre-gelatinized starches and dextrose, hydroxypropylmethylcellulose, hydroxypropylcellulose, ethylcellulose, gum arabic, tragacanth and guar gum.

9. The pharmaceutical composition of claim 1 wherein the pharmaceutical agent is selected from selegiline and its acid addition salts.

10. The pharmaceutical composition of claim 7 wherein the pharmaceutical agent is selected from selegiline and its acid addition salts.

* * * * *

UNITED STATES PATENT AND TRADEMARK OFFICE
CERTIFICATE OF CORRECTION

PATENT NO. : 5,484,608
DATED : January 16, 1996
INVENTOR(S) : Edward M. Rudnic, John A. McCarty and George W. Belenduik It is certified that error appears in the above-identified patent and that said Letters Patent is hereby corrected as shown below:

Column 1,
Line 16, after "less" change "pans" to -- parts --
Line 16, after "one" change "pan" to -- part --
Lines 18 and 20, change "pans" to -- parts --
Line 21, change "pan" to -- part --

Signed and Sealed this

Third Day of February, 2004

JON W. DUDAS
*Acting Director of the United States Patent and Trademark Office*